ized product.

United States Patent [19]

Pourreau et al.

[11] Patent Number: 5,130,451
[45] Date of Patent: Jul. 14, 1992

[54] PROCESS FOR PREPARING CARBOXYARYL PHOSPHATES

[75] Inventors: Daniel B. Pourreau, Aurora; John J. Bailey, Clarendon Hills, both of Ill.

[73] Assignee: Amoco Corporation, Chicago, Ill.

[21] Appl. No.: 677,639

[22] Filed: Mar. 28, 1991

[51] Int. Cl.$^5$ .............................................. C07F 9/12
[52] U.S. Cl. ................................................... 558/198
[58] Field of Search ......................................... 558/198

[56] References Cited

U.S. PATENT DOCUMENTS 3,666,840  5/1972  Ito et al. .............................. 558/198

Primary Examiner—Richard L. Raymond
Attorney, Agent, or Firm—Thomas E. Nemo; William H. Magidson; Frank J. Sroka

[57] ABSTRACT

A process is disclosed for the liquid phase oxidation of aryl phosphates having at least one oxidizable substituent on at least one aryl moiety, wherein the oxidizable substituent is oxidized to a carboxylic acid substituent. Staged addition of the oxidation catalyst provides for improved yields of oxidized product.

22 Claims, No Drawings

PROCESS FOR PREPARING CARBOXYARYL PHOSPHATES

FIELD OF THE INVENTION

This invention relates generally to a process for preparing carboxyaryl phosphates. More particularly, this invention concerns an improved process for preparing carboxyaryl phosphates where an aryl phosphate feedstock having at least one oxidizable substituent on at least one aryl moiety is catalytically oxidized in a liquid phase oxidation reaction to transform the oxidizable substituent to a carboxylic acid substituent.

BACKGROUND OF THE INVENTION

Phosphates, particularly aryl phosphates, are useful materials. These compounds do not burn easily and, in fact, many are self-extinguishing. Aryl phosphates are widely used as additives in polymeric materials as flame retardants and as plasticizers.

Carboxyaryl phosphates, i.e., an aryl phosphate wherein at least one aryl moiety is substituted with a carboxylic acid group, are also useful materials. For example, U.S. Pat. No. 3,666,840 to Ito et al. describes a class of polycarboxylic triphenyl phosphates and teaches that these materials have a number of desirable properties such as high melting points and heat stability. They are also described as being non-flammable and self-extinguishing. Because of these properties, it is taught by Ito et al. that carboxyaryl phosphates are particularly suitable as constituents of synthetic resins, synthetic fibers and other high polymer substances which are required to be heat resistant and fire resistant, and as various processing agents for imparting fire resistance or flame resistance to common synthetic resins, and natural and synthetic fibers. These phosphates are also a convenient source of various hydroxyphenyl carboxylic acids since the phosphate ester bond may be hydrolyzed to release a hydroxyphenyl carboxylic acid.

The Ito et al. patent also describes a process for preparing polycarboxytriphenyl phosphates by oxidizing the corresponding polymethyl triphenyl phosphates in a liquid phase oxidation reaction using an oxygen-containing gas and a catalyst containing vanadium, chromium, manganese, cobalt, nickel, copper or molybdenum. Cocatalysts and/or promoters such as halides, organic carbonyl compounds, peroxides and ozone are also taught as being advantageous if used in combination with the metal catalysts. The process disclosed in Ito et al., however, is impractical and would not be desirable, for example, in a commercial-scale operation. In all of the examples provided therein the reaction time for oxidizing the disclosed polymethyl triphenyl phosphates is on the order of 3 to 13 hours, and, furthermore, the specification states that reaction conditions should be chosen so that the reaction is substantially complete within a period ranging from 4 to 24 hours, excluding the induction period. These reaction times are generally too long to be useful for a commercial-scale manufacturing operation.

An improved process for preparing carboxyaryl phosphates, a process suitable for a commercial-scale manufacturing operation, would be desirable. The present invention provides such an improved process.

SUMMARY OF THE INVENTION

Provided is a liquid phase process for oxidizing an aryl phosphate having at least one oxidizable substituent on at least one aryl moiety, which process comprises reacting said phosphate with a source of molecular oxygen under substantially anhydrous conditions in a reaction mixture comprising a heavy metal catalyst and a solvent comprising a lower aliphatic carboxylic acid; at a pressure sufficient to maintain said reaction mixture substantially in the liquid phase; and at an elevated temperature and for a time sufficient to oxidize at least a portion of said oxidizable substituent to an aromatic carboxylic acid substituent; a first portion of said catalyst being charged to said reaction mixture initially to initiate said reacting, and the remaining portion of said catalyst being added to said reaction mixture during said reacting. The disclosed process wherein the catalyst addition to the reaction mixture is staged provides for the preparation of carboxyaryl phosphates in high yield and in short reaction times. The disclosed process allows the oxidation reaction to be conducted at elevated temperatures without the hydrolysis or decomposition of the desired product.

DETAILED DESCRIPTION OF THE PREFERRED EMBODIMENTS

The present invention is a rapid and efficient process for oxidizing aryl phosphates wherein the aryl moiety contains an oxidizable substituent and wherein the oxidizable substituent is oxidized to a carboxylic acid substituent. The carboxyaryl phosphates produced by the process of this invention are useful as additives for a variety of high polymer, elastomer and natural and synthetic resins and fibers requiring heat resistance and fire retardance. For example, the carboxyaryl phosphates produced by the process of this invention can be used in formulations with polyarylates, polyarylethers such as polyarylether sulfones and polyarylether ketones, polyamides, polyamideimides, polyetherimides and polycarbonates.

In the invented process, the phosphate feedstock having an oxidizable substituent is oxidized in the liquid phase using molecular oxygen and catalyzed by a heavy metal catalyst. The oxidation reaction is conducted at an elevated temperature and at a pressure sufficient to maintain the reaction mixture substantially in the liquid phase. Although a number of heavy metal catalysts are useful, cobalt in combination with manganese is preferred, particularly when used with a bromine promoter. It is also necessary to conduct the oxidation reaction under substantially anhydrous conditions. One suitable method for maintaining anhydrous conditions is to include a dehydrating agent in the reaction mixture. It is believed that the dehydrating agent reacts with or absorbs water formed during the oxidation reaction and thereby prevents the water from reacting with the phosphates. The water can hydrolyze the phosphate ester bonds and form phenols. Phenols are known oxidation inhibitors and their presence in the reaction mixture is undesirable. It has also been determined that the addition of the metal catalyst during the course of the oxidation reaction, rather than adding all the catalyst initially, unexpectedly improves the reaction yield. The process of this invention also provides for a rapid reaction making this process suitable for commercial production.

The aryl phosphate feedstock suitable for the oxidation process of this invention is any aryl phosphate having at least one aryl moiety substituted with at least one oxidizable substituent. The aromatic moiety may, for example, be phenyl, biphenyl, naphthyl, or other polycylic aromatic moiety. Preferably the aromatic moiety is phenyl. The oxidizable substituent is a hydrocarbyl group, preferably a lower alkyl containing 1 to about 4 carbon atoms, i.e., a $C_1$–$C_4$ alkyl. The hydrocarbyl group may be saturated, unsaturated, branched, or cyclic. The oxidizable substituent may also be a partially oxidized hydrocarbyl such as, for example, an alcohol, ketone, aldehyde or ether. The oxidizable substituent may also be a halogenated alkyl wherein the halogen is preferably chlorine or bromine. Due to availability and cost, the oxidizable substituent is preferably methyl, ethyl or isopropyl, more preferably methyl or ethyl, and most preferably methyl.

The aryl phosphates useful as feedstocks for the process of this invention include the monoaryl, diaryl and triaryl esters of orthophosphoric acid. For example, monoaryl orthophosphates, monoalkyl-monoaryl orthophosphates, diaryl orthophosphates, dialkyl-monoaryl orthophosphates, monoalkyl-diaryl orthophosphates and triaryl orthophosphates are suitable feedstocks, providing at least one aryl moiety contains at least one oxidizable substituent. The aryl moiety can be phenyl, biphenyl, naphthyl or other polycyclic aromatic group. Where the feedstock is diaryl or triaryl, the aryl moieties may be the same or different.

A presently preferred class of aryl phosphate feedstocks suitable for use in the method of this invention comprises those triaryl phosphate esters having the structure (I) below:

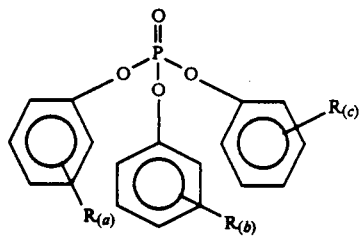

(I)

where a, b and c are each independently a number from 0 to 5, preferably 0 to 2, inclusive, and where (a+b+c) is at least 1. For each phenyl moiety and within each phenyl moiety R is independently selected from the group consisting of methyl, ethyl and isopropyl. More preferably R is independently methyl or ethyl. Most preferably R is methyl.

A highly preferred aryl phosphate feedstock is a mixture of aryl phosphates known in the flame retardant and plasticizer arts as TCP or tricresyl phosphate. TCP is prepared by the reacting cresylic acids with phosphorus oxychloride. TCP is available commercially under the tradenames, Celluflex, Kronitex and Lindol. TCP is available from, for example, FMC Corporation, Nitro, W. Va. Ciba Geigy manufactures a product called Pliabrac TCP ™ which is available from Albright & Wilson, Inc., Richmond, Va., and is listed in the published Material Safety Data Sheet as tricresyl phosphate. Generally, to avoid toxicity problems, the cresylic acid used to make TCP is very low in ortho-substituted isomer.

Other aryl phosphates suitable for use as a feedstock in the process of this invention include cresyl diphenylphosphate, isopropylphenyl diphenylphosphate, tri-meta-tolylphosphate (tri-meta-cresylphosphate), tri-para-tolylphosphate (tri-para-cresylphosphate), diphenyl meta-tolylphosphate, diphenyl para-tolylphosphate, phenyl di-meta-tolylphosphate, phenyl di-para-tolylphosphate, phenyl dicresylphosphate, and the like.

The carboxyaryl phosphates prepared by the process of this invention can have one or more carboxylic acid substituents per molecule depending on the aryl phosphate feedstock and the degree of oxidation. For example, where the feedstock molecule contains only one oxidizable substituent, a monocarboxylic acid product will be produced. However, where the phosphate feedstock molecule contains more than one oxidizable substituent, the product carboxylic acid may be a polycarboxylic acid wherein all of the oxidizable substituents are oxidized, or the product may be partially oxidized such that less than all of the oxidizable substituents are oxidized to carboxylic acids. Preferably, however, the aryl phosphate feedstock is oxidized such that substantially all of the oxidizable substituents are converted to a carboxylic acid substituent. For example, when the phosphate feedstock is tri-para-cresylphosphate, the desired oxidized product is 4,4',4''-tricarboxytriphenylphosphate, and when the feedstock is tri-meta-cresylphosphate, the desired oxidized product is 3,3',3''-tricarboxytriphenylphosphate. When TCP is a feedstock for the process of this invention, the product formed is a complex mixture of carboxyaryl phosphates. This is because the TCP itself is a complex mixture. However, the degree of oxidation of the TCP can be quantified, for example, by measuring the Total Acid Number (TAN) of the oxidized product.

In the process of this invention the solvent used for oxidizing the phosphates comprises a $C_2$–$C_6$ aliphatic monocarboxylic acid, or mixtures thereof. Due to cost and availability, acetic acid is preferred. In addition to the aliphatic monocarboxylic acid solvent, the oxidation reaction solvent can contain other solvents such as benzene, chlorinated aromatics, halogenated alkanes, and the like. The weight ratio of solvent to aryl phosphate feedstock is suitably at least about 2:1, respectively, and more preferably at least 4:1. Most preferably the weight ratio of solvent to feedstock is in the range of about 4:1 to about 10:1, the solvent being either an aliphatic monocarboxylic acid or a mixture of aliphatic monocarboxylic acid and one or more other solvents.

The source of molecular oxygen employed in the oxidation of the phosphate ester may vary in molecular oxygen content from about 1% to about 100% oxygen. When the oxygen content is less than 100%, another gas, such as nitrogen, is used for the balance. Air is the presently preferred source of molecular oxygen. The source of oxygen-containing gas should be delivered to the oxidation reaction mixture at a rate such that the oxidation reaction has sufficient molecular oxygen available for the oxidation reaction to proceed without the oxygen concentration limiting the reaction rate, i.e., oxygen starvation.

The oxidation catalyst employed in the process of this invention is a heavy metal catalyst comprising one or more metals having an atomic number ranging from 21 to 82, inclusive. The metal should be in a form that is initially soluble in the reaction mixture or that becomes soluble soon after being introduced into the reaction mixture. Suitable catalyst metals include, for example, cobalt, manganese, nickel, chromium, cerium, copper, palladium and mixtures thereof such as cobalt and manganese. The presently preferred oxidation catalyst comprises a mixture of cobalt and manganese metal components and a bromine promoter component, each in an amount in the reaction mixture sufficient to provide for the oxidation of the oxidizable substituents on the aryl phosphate feedstock to carboxylic acid substituents. In the preferred catalyst comprising cobalt, manganese and bromine components, the weight ratio of cobalt (calculated as elemental cobalt) in the cobalt component of the catalyst-to-phosphate feedstock is preferably in the range of about 0.2 to about 100, more preferably about 10 to 75, and most preferably about 20 to about 60 milligram atoms (mga) per gram mole of aryl phosphate feedstock. The weight ratio of manganese (calculated as elemental manganese) in the manganese component of the catalyst-to-cobalt (calculated as elemental cobalt) in the cobalt component of the catalyst is preferably in the range of about 0.2 to about 10 mga per mga of cobalt. The weight ratio of bromine (calculated as elemental bromine) in the bromine promoter component of the catalyst-to-total cobalt and manganese (calculated as elemental cobalt and elemental manganese) in the cobalt and manganese components of the catalyst is preferably in the range of about 0.2 to about 2.0 mga per mga of total cobalt and manganese. When using the catalyst comprising cobalt, manganese and bromine components, a cerium and/or zirconium component may also be added, each being used in a weight ratio (calculated as elemental cerium or zirconium) of about 0.01 to about 1.0 mga per mga of cobalt (calculated as elemental cobalt). Nickel can be used to replace some or all of the cobalt in the preferred cobalt and manganese catalyst, and cerium can replace some or all of the manganese. The amounts of catalyst metals and bromine promoter described above are those amounts that are present in the reaction mixture at the end of the oxidation reaction or, if a continuous process is used, at the last stage of the oxidation reaction. Each of the catalyst metals referred to hereinabove may be provided in any of their known ionic or combined forms providing, as already mentioned, the metal is soluble or becomes soluble in the reaction mixture. For example, when the solvent is an acetic acid medium and the catalyst metals include cobalt and manganese, cobalt and/or manganese carbonate, acetate tetrahydrate, and/or bromide can be employed.

When bromine is used, the bromine-to-total cobalt and manganese milligram atom ratio in the range of about 0.2:1.0 to about 2.0:1.0 can be satisfied by the addition to the reaction mixture a suitable source of bromine. Such bromine sources include elemental bromine ($Br_2$), ionic bromine (for example, HBr, NaBr, KBr, $NH_4Br$, and the like), or organic bromides which provide bromide ions at the operating temperature of the oxidation reaction (for example, benzylbromide, mono- and dibromo acetic acid, bromoacetyl bromide, tetrabromoethane, ethylene dibromide, and the like). The total bromine in molecular bromine and ionic bromide is used to determine satisfaction of the preferred elemental bromine-to-total cobalt and manganese milligram atom ratio of about 0.2:1.0 to about 2.0:1.0.

Although it is not necessary to stage the addition of the catalyst metals to the reaction mixture when a catalyst comprising cobalt and manganese and a bromine promoter component is used in the process of this invention, best results were obtained when the addition of these catalyst metals was staged. Similarly, when the other aforementioned catalyst metals are employed it is most advantageous to stage their addition to the reaction mixture. Catalyst metal staging results in unexpectedly higher reaction yields. By staging the addition of these metals it is meant that a portion of the total charge of catalyst metal or metals is added initially to the reaction mixture to initiate the oxidation reaction at the given reaction temperature and pressure, then the remaining portion of the total catalyst metal charge is added during the course of the oxidation reaction. Stated another way, staging means adding at least a portion of the catalyst to the reaction mixture during the oxidation reaction. When more than one catalyst metal is used, the staging of the catalyst metals includes adding a portion of each of the catalyst metals during the reaction or adding only one or more but less than all of the metals. For example, in an oxidation reaction catalyzed by cobalt and manganese, both the cobalt and manganese together can be added to the reaction mixture during the oxidation reaction to effect the staging. Alternatively, only the cobalt or only the manganese can be added in a staged manner. Similarly, a bromine component can be added in a staged manner when used with cobalt and manganese, either with or without the staged addition of cobalt and manganese. Preferably, when the oxidation catalyst comprising cobalt and manganese metal components and a bromine promoter component is used, a portion of the catalyst composition comprising a mixture of cobalt, manganese and bromine is added initially, and the remaining portion of the mixture of cobalt, manganese and bromine is added during the course of the oxidation reaction. When staging the addition of the catalyst, or only one component of the catalyst, the addition can be in one or more discrete additions or, more conveniently, the addition is completed in a continuous manner at a fixed or constant addition rate. A solvent, such as the reaction solvent, is advantageously used in the staged addition of the catalyst. A solution of the catalyst is much easier to add to the reaction mixture in a controlled manner using one or more suitable means for delivering a liquid phase to a reaction mixture at a controlled rate. A piston pump is one such suitable means.

Preferably about 0.1 to about 80, more preferably about 5 to about 50 and most preferably about 10 to about 30 weight percent of the total catalyst charge is added initially to the reaction mixture with the remaining portion being added to the reaction mixture during the course of the oxidation reaction.

In the oxidation process of this invention, it is necessary to maintain substantially anhydrous conditions in the reaction mixture. One suitable means to maintain anhydrous conditions is to use a dehydrating agent, i.e. a reagent that absorbs or reacts with water to remove the water from the reaction mixture. Another suitable means is to remove the water by a distillation procedure where the water is distilled from the reaction mixture as the water is formed. The water requiring removal is either water initially present in the reaction mixture, or water that is formed during the oxidation reaction as the oxidizable substituent is oxidized to a carboxylic acid thereby forming carbon oxides and water. For example, when acetic acid is used as a reaction solvent there is typically present a certain amount of water in the acetic acid. Glacial acetic acid, a common source of acetic acid, generally contains about 0.2% water. Although not wishing to be bound by a theory of operation, it is believed that the water, if present to a significant extent in the reaction mixture, can react with the aryl phosphate feedstock molecule or carboxyaryl phosphate product molecule to hydrolyze the phosphate ester bond and form a phenolic compound. Phenolic compounds are known oxidation inhibitors and may suppress or completely arrest the oxidation reaction. The dehydrating agents suitable for use in the method of this invention include any agent that will physically absorb or chemically react with water so as to effectively remove the water from the reaction mixture. Another requirement is that the dehydrating agent not adversely affect the oxidation reaction, e.g. poison the catalyst. Suitable dehydrating agents, for example, include anhydrides of mineral acids such as phosphorus pentoxide and sulfur trioxide, anhydrides of organic carboxylic acids, preferably anhydrides of those carboxylic acids having about 2 to about 8 carbon atoms, inclusive, per molecule, and molecular sieves such as 3A and 4A that absorb water but do not absorb significantly larger molecules. The anhydrides of organic carboxylic acids having about 2 to about 6 carbon atoms per acid molecule are the presently preferred dehydrating agents for the oxidation process of this invention. Among the anhydrides of organic carboxylic acids having about 2 to about 6 carbon atoms per molecule of carboxylic acid, the most highly preferred carboxylic acid anhydride is the anhydride corresponding to the aliphatic carboxylic acid used in the solvent for the oxidation reaction. Thus, if acetic acid is used in the reaction solvent, acetic anhydride is the preferred anhydride. In addition to removing water from the reaction mixture, anhydrides of organic acids most likely acylate any phenolic compounds that may form in the oxidation reaction mixture or that are already present in the reaction mixture as an impurity in the aryl phosphate feedstock, thereby removing the free phenolic compounds as potential oxidation inhibitors. The dehydrating agent may be added to the reaction mixture all at once initially, or it may be added during the course of the oxidation reaction. The amount of dehydrating agent is preferably an amount that provides for the rapid removal of the water in the reaction mixture. On a weight basis, the dehydrating agent can be in the range of about 1 to about 95 percent of the total reaction mixture. For example, when a liquid aliphatic acid anhydride such as acetic anhydride is used as the dehydrating agent, it can function as part of the reaction solvent and can be present in an amount of about 1 to about 99 weight percent of the reaction solvent, more preferably about 5 to about 50 weight percent of the oxidation reaction solvent. When an acid anhydride is used as the dehydrating agent, it is most preferred to add the anhydride to the oxidation reaction mixture at about the same rate as the production of water. This preferred procedure reduces the burning of the anhydride.

The pressure for the oxidation process of this invention is a pressure sufficient to maintain a substantial portion of the reaction mixture, preferably at least about 70%, in the liquid phase at the temperature used for the oxidation reaction. The pressure may range from subatmospheric to superatmospheric. Preferably, the pressure is in the range of about 0.1 atmosphere to about 50 atmospheres, more preferably about 1 to about 25 atmospheres. The reaction temperature is any temperature that will allow the oxidation to proceed at a rapid rate. Preferably, the reaction temperature is in the range of about 200° F. to about 500° F., more preferably about 350° F. to about 450° F. A particularly preferred reaction temperature is in the range of about 395° F. to about 450° F. When the reaction temperature is in this particularly preferred range the reaction is most rapid and high yields of the desired carboxylic acid products are obtained. The reaction rate and overall reaction time, will, of necessity, be a function of the types and amount of catalyst used, the type and purity of the aryl phosphate feedstock, particularly the nature of the oxidizable substituent on the aryl ester group and the size, i.e., scale, of the reaction. Due to the high rates of reaction made possible by the process of this invention, residence times for commercial-scale processes of about 20 minutes to about 120 minutes are possible.

At the end of the oxidation reaction, depending on the amount and type of solvent selected and the product formed, the carboxyaryl phosphate product may either precipitate from the reaction mixture as a solid or may require isolation by one or more suitable methods. It is desirable to have the product precipitate from the reaction mixture because it can then be easily and efficiently removed by filtration, settling, centrifugation or other suitable means for separating a solid from a liquid component. The solid product may subsequently be washed with one or more suitable solvents such as an aliphatic carboxylic acid, water or mixtures thereof. When the product is soluble in the reaction mixture, however, or when the product itself is not a solid, the presently preferred method for recovering the product comprises adding water to the reaction mixture, either with or without first reducing the amount of oxidation solvent in the reaction mixture by, for example, distillation or evaporation, and then extracting the desired product by contacting the resulting mixture with a solvent immiscible with water. Suitable solvents for this extraction include, benzene, alkyl aromatics such as toluene, xylene, $C_9$ aromatics, or mixtures thereof; halogenated solvents such as dichloromethane, chloroform, carbon tetrachloride, dichloroethane and trichloroethane; hydrocarbon solvents such as hexanes, naphthas, cyclohexane and other aliphatic or cycloaliphatic compounds; ethers such diethylether and tetrahydrofuran; ketones such as acetone and methylethyl ketone; and any other organic solvent that is immiscible with water. Preferably the solvent also has a high solubility for the carboxyaryl phosphate product and preferably the solvent is volatile so that it can be easily eliminated if desired.

Once the extraction is completed, the solution is optionally dried to remove excess water and typically filtered to remove any particulates. Preferably the extraction solvent is removed by any suitable means such as evaporation or distillation, typically at reduced pressure, to produce the desired product. Also, either before or after removal of some of the extraction solvent, the solution may be cooled to induce crystallization of solid product which can be easily recovered.

The oxidation method of this invention may be conducted in the batch, semi-continuous or continuous mode. By "batch" it is meant that all of the aryl phosphate feedstock is added to the reaction mixture initially. By "semi-continuous", it is meant that some or all of the phosphate ester feedstock is added to the reaction mixture during the oxidation reaction. By "continuous" it is meant the feedstock along with other reaction mixture components such as solvent and dehydrating agent are added continuously to the reaction zone and a product mixture is continuously removed from the reaction zone. For a continuous process, the staging of the catalyst requires, for example, at least two separate reactor vessels, or some other suitable means of adding catalyst in stages to the reaction mixture.

The following examples are presented to illustrate the present invention without intending to limit the scope thereof.

EXAMPLE 1

Oxidation of m-TCP (tri-meta-cresylphosphate)

To a one-liter stirred titanium autoclave reactor vessel was charged 2.00 grams Co(OAc)$_2$.4H$_2$O, 2.00 grams Mn(OAc)$_2$.4H$_2$O, 1.58 grams NH$_4$Br, 300 grams glacial acetic acid, 50 grams acetic anhydride and 50 grams of 97% tri-meta-cresylphosphate (practical grade). The reactor was sealed and the contents heated to 380° F. under a nitrogen atmosphere. The oxidation was started by switching from nitrogen to an air flow of approximately 12 cu-ft/hr. During the course of the oxidation reaction, acetic anhydride was pumped into the reaction mixture at a rate of approximately 1.75 ml/minute. Table 1 below provides the vent gas composition from the autoclave reactor as a function of reaction time (minutes), temperature (°F.) and pressure (psig). At the end of the reaction, no solids were observed in the reactor effluent. The data in Table 1 however indicates that the oxidation reaction proceeded for approximately 25 minutes i.e., this is the time it took for the oxygen concentration in the vent gas to reach approximately that of air.

TABLE 1

| Time | Temp. | Pressure | % O$_2$ | % CO$_2$ | % CO |
|---|---|---|---|---|---|
| 0 | 380 | 300 | 0 | 0 | 0 |
| 3 | 402 | 340 | 0 | 0 | 0 |
| 5 | 410 | 340 | 0.2 | 0.68 | 0.62 |
| 8 | 408 | 340 | 0.5 | 2.95 | 1.91 |
| 10 | 403 | 340 | 0.5 | 4.15 | 2.40 |
| 13 | 400 | 340 | 2.5 | 4.75 | 2.35 |
| 15 | 390 | 340 | 8.4 | 3.65 | 1.41 |
| 18 | 382 | 340 | 16.5 | 1.40 | 0.49 |
| 20 | 370 | 340 | 19.2 | 0.75 | 0.27 |
| 25 | 370 | 340 | 20.8 | 0.35 | 0.20 |

The procedure of Example 1 was repeated except that 1.12 grams of sodium acetate were included in the reaction mixture. The acetate did not appear to improve the oxidation reaction although it was still added in subsequent reactions. Oxygen was consumed for approximately 35 minutes. Again, solids were not isolated from the reactor effluent.

EXAMPLE 2

Oxidation of m-TCP (tri-meta-cresylphosphate)-Staged Catalyst Addition

To a one-liter stirred titanium autoclave reactor vessel was charged 0.500 gram Co(OAc)$_2$.4H$_2$O, 0.493 gram Mn(OAc$_2$).4H$_2$O, 0.412 gram NH$_4$Br, 300.0 grams glacial acetic acid, 50.0 grams acetic anhydride, 50.0 grams of tri-meta-cresylphosphate and 0.51 gram NaOAc. A second mixture was prepared by adding 3.5 grams Co(OAc$_2$).4H$_2$O, 3.5 grams Mn(OAc$_2$).4H$_2$O, 2.50 grams NH$_4$Br, and 1.56 grams NaOAc to 125 grams of acetic acid and 125 grams of acetic anhydride. The reactor was sealed and the contents heated to 400° F. under nitrogen. The reaction was started by switching to an air flow of approximately 12 cu-ft/hr. During the course of the reaction the second mixture was pumped into the reactor at a rate of approximately 4.0 ml/minute using a piston pump. Table 2 below provides the vent gas composition as a function of reaction time, temperature and pressure. At the end of the reaction a large amount of tan-colored precipitate formed in the cooled reactor effluent and was collected by filtration. The solid product weighed 38.9 grams and was characterized as 3,3',3"-tricarboxytriphenylphosphate using proton, carbon and phosphorus nuclear magnetic resonance spectroscopy.

TABLE 2

| Time | Temp. | Pressure | % O$_2$ | % CO$_2$ | % CO |
|---|---|---|---|---|---|
| 0 | 400 | 320 | 0 | 0 | 0 |
| 3 | 401 | 320 | 0 | 0 | 0 |
| 5 | 407 | 320 | 0.3 | 0.50 | 0.64 |
| 8 | 400 | 320 | 0.4 | 1.65 | 1.46 |
| 10 | 400 | 320 | 0.4 | 2.40 | 1.70 |
| 13 | 403 | 320 | 0.4 | 3.45 | 1.70 |
| 15 | 397 | 320 | 0.5 | 4.80 | 1.88 |
| 18 | 394 | 320 | 13.5 | 2.05 | 0.66 |
| 20 | 398 | 320 | 16.6 | 1.05 | 0.33 |
| 25 | 408 | 320 | 19.5 | 0.40 | 0.13 |
| 30 | 400 | 320 | 20.5 | 0.20 | 0.09 |

Examples 1 and 2 demonstrate that tri-meta-cresylphosphate is effectively oxidized to the corresponding tricarboxylic acid by the process of this invention. The staged catalyst addition of Example 2 provided for a superior product which was easily isolated by filtration from the oxidation mother liquor. Both oxidations were completed in about 30 minutes.

EXAMPLE 3

Oxidation of m-TCP(tri-meta-cresylphosphate)-Staged Catalyst and Semi-continuous Addition of m-TCP To a one-liter titanium autoclave reactor was charged a mixture of 0.50 gram Co(OAc)$_2$.4H$_2$O, 0.48 gram Mn(OAc)$_2$.4H$_2$O, 0.41 gram NH$_4$Br, 0.45 gram NaOAc, 250 grams glacial acetic acid, and 50.0 grams acetic anhydride. A reservoir for a piston pump was charged with a second mixture containing 1.5 grams Co(OAc)$_2$.4H$_2$O, 1.5 grams Mn(OAc)$_2$.4H$_2$O, 1.10 grams NH$_4$Br, 0.85 gram NaOAc and 65 grams of 97% tri-meta-cresylphosphate (practical grade), all dissolved in 80 grams of acetic anhydride.

The autoclave contents were heated to 385° F. at a pressure of 310 psig under a flow of nitrogen gas. Once a temperature of 385° F. was attained the gas flow was switched to air at a flow rate of 18 cu-ft./hr. The piston pump was started and the second mixture was pumped into the autoclave. The flow rate of the piston pump and the air rate were adjusted during the oxidation to stabilize the oxygen vent gas concentration to a target level of about 5%. Reaction temperature was maintained at 400° F. with the use of internal reactor cooling coils. The oxidation reaction was vigorous during the initial 9 minutes of the reaction with an oxygen vent gas concentration of less than 2%. During the period from 9 to 18 minutes the oxygen vent gas concentration stabilized at 10%. The piston pump was stopped after 18 minutes when the desired 50 gram charge of tri-m-cresylphosphate was added. The oxygen vent gas concentration then increased at a steady rate and reached 20.9% after a total of 30 minutes, at which time the inlet gas was switched to nitrogen.

The dark colored reactor effluent was cooled to room temperature overnight and the solids formed were collected by filtration. The solid product was washed with water and dried. The isolated product weighed 52.0 grams. Analysis by proton, phosphorus ($^{31}$P) and carbon ($^{13}$C) nuclear magnetic resonance spectroscopy demonstrated that the product was 3,3',3"-tricarboxytriphenylphosphate. The elemental analysis results for carbon (C), hydrogen (H), oxygen (O) and phosphorus (P) for the combined products produced from this reaction and similarly conducted oxidation reactions are as follows: actual %:(theoretical % for 3,3',3"-tricarboxy-tri-phenylphosphate)] C 53.6:(55.0), H 3.5:(3.3), O 32.4:(34.9), P 5.8:(6.8). The yield was 83.9%.

This example demonstrates that a high yield of 3,3',3"-tricarboxy-triphenylphosphate that can be obtained by the method of this invention. In this example, a semi-continuous addition of the feedstock was used which appears to have increased the overall yield of the carboxylic acid product.

EXAMPLE 4

Oxidation of m-TCP (Tri-meta-cresylphosphate)-No Acetic Anhydride

The procedure of Example 2 was repeated without the addition of acetic anhydride to either the initial reactor charge or to the second mixture. The reaction was terminated after 30 minutes. The reaction time-vent gas oxygen profile indicated that the oxidation reaction did not proceed to a significant extent. This example demonstrates that an anhydrous reaction conditions are required for the oxidation process of this invention.

EXAMPLE 5

Oxidation of p-TCP (Tri-para-cresylphosphate)-Staged Catalyst Addition

The one-liter autoclave used in the previous examples was charged with a mixture of 0.5 gram $Co(OAc)_2.4H_2O$, 0.5 gram $Mn(OAc)_2.4H_2O$, 0.42 gram $NH_4Br$, 0.5 gram NaOAc, 50 grams of tri-para-cresylphosphate, 300 grams of glacial acetic acid and 50 grams of acetic anhydride. A reservoir for a piston pump was charged with a second mixture of 1.5 grams $Co(OAc)_2.4H_2O$, 1.5 grams $Mn(OAc)_2.4H_2O$, 1.02 grams $NH_4Br$, and 1.01 grams NaOAc in 100 grams of acetic anhydride.

The autoclave contents were heated to 395° F. at a pressure of 310 psig under a flow of nitrogen gas. Once a temperature of 395° F. was attained the gas flow was switched to air at a flow rate of 13 cu-ft/hr, and the piston pump was started and the second mixture pumped into the autoclave at a rate of approximately 3 ml/minute. The reaction temperature was maintained at 400° F. throughout the oxidation using internal reactor cooling. The oxidation reaction was vigorous for the first 14 minutes with the oxygen vent gas concentration remaining below 1%. After 15 minutes the oxygen vent gas concentration increased rapidly and the piston pump flow rate was increased to 6 ml/minute. After 27 minutes from the initiation of the reaction (i.e. when air was first added) the oxygen vent gas concentration reached 20.9% and the oxidation reaction was terminated by switching the air flow back to nitrogen gas. The dark brown homogeneous reactor effluent was allowed to cool to room temperature overnight and the solids formed were separated from the liquid by filtration. The solid product was washed with water and air dried.

The isolated product weighted 31.0 g. The filtrate was treated with 1 liter of distilled water and extracted three times with approximately 150 milliliters of chloroform. The chloroform extracts were separated from the aqueous layer, combined, and dried over magnesium sulfate. Evaporation of the chloroform under reduced pressure produced another 12.6 grams of product. Analysis of the product by proton, phosphorus, and carbon nuclear magnetic resonance spectroscopy demonstrated that the product was 4,4',4"-tricarboxy-triphenylphosphate with no significant impurities present. The averaged elemental analysis results for the two products are as follows: actual %: (theoretical % for 4,4',4"-tricarboxy-triphenylphosphate) C 53.6:(55.0), H 3.5:(3.3), O 32.6:(34.9), P 6.1:(6.8). Overall yield was 70.3%.

This example illustrates that tri-para-cresylphosphate is effectively oxidized by the method of this invention. This example also illustrates the preferred product recovery process of this invention wherein product that has not crystallized from the reaction mixture can be effectively recovered by first adding water to the reactor effluent followed by extraction with a suitable water-immiscible solvent.

EXAMPLE 6

Oxidation of TCP Mixture - Staged Catalyst Addition and Semi-Continuous Addition of TCP Mixture The one-liter autoclave described in the previous examples was charged with 0.5 gram $Co(OAc)_2.4H_2O$, 0.5 gram $Mn(OAc)_2.4H_2O$, 0.42 gram $NH_4Br$, 0.5 gram NaOAc, 5.0 grams of commercial tricresylphosphate (Pliabrac TM TCP), 300 grams of glacial acetic acid and 50 grams of acetic anhydride. A reservoir for a piston pump was charged with a second mixture containing 1.5 grams $Co(OAc)_2.4H_2O$, 1.5 grams $Mn(OAc)_2.4H_2O$, 1.02 grams $NH_4Br$, and 0.85 gram NaOAc, and 45 grams tricresylphosphate (Pliabrac TM TCP) dissolved in 100 grams of acetic anhydride. A third mixture was prepared identical to the mixture charged to the autoclave except there was no tricresylphosphate present and 100 grams rather than 50 grams of acetic anhydride were added. The contents of the autoclave were heated to 385° F. at a pressure of 320 psig under a flow of nitrogen gas. The oxidation reaction was started by switching the nitrogen flow to an air flow of 20 cu-ft/hr and immediately beginning the addition of the second mixture through the piston pump. The temperature of the reaction was maintained at 400° F. using internal reactor cooling. The piston pump ran initially at 4 ml/minute and was increased to 8 ml/minute after 5 minutes. The air rate was reduced to 17 cu-ft/hr at this time and the oxygen vent gas concentration stabilized between 13 and 15% until the desired tricresylphosphate feedstock charge was added, i.e., 20 minutes. The third mixture was added to the piston pump reservoir and added to the autoclave at a rate of 2-3 ml/minute for 35 minutes. The oxygen vent gas level increased to 19% where it remained for 75 minutes. After 90 minutes total, the oxygen vent gas concentration reached 20.9% at which time the oxidation reaction was stopped by switching to a nitrogen gas flow. The effluent from the autoclave was collected and treated as described in Example 5 except that no solids were collected by filtration. Based on analysis by proton, phosphorus and carbon nuclear magnetic resonance spectroscopy, the composition of the liquid product mixture was consistent with a mixture of trialkylphosphates where the alkyl aromatic substituents have been oxidized to carboxylic acid groups thereby forming carboxyphenylphosphates.

The product weighted 54.5 grams and the Acid Number was 236.3 mg KOH/gram. The elemental analyses for carbon, hydrogen, oxygen and phosphorus are as follows:

|   | C | H | O | P |
|---|---|---|---|---|
| Feedstock | 68.7 | 6.0 | 17.1 | 8.3 |
| Product | 59.4 | 4.6 | 29.2 | 5.1 |

EXAMPLE 7

Oxidation of TCP Mixture - No Catalyst Staging

A mixture of 50 grams of commercial tricresylphosphate (Pliabrac TM TCP) was oxidized in a manner similar to that described in Example 6, however, the catalyst and tricresylphosphate feedstock were added to the autoclave reactor all at once. The catalyst and solvent mixture was 4.0 grams $Co(OAc)_2.4H_2O$, 4.0 grams $Mn(OAc)_2.4H_2O$, 3.13 grams $NH_4Br$, 400 grams of glacial acetic acid and 30 grams of acetic anhydride. The reaction temperature was approximately 400° F. and the pressure 400 psig. The oxidation reaction proceeded for 65 minutes.

The liquid product weight 35.9 grams. The Acid No. was 189.9 mg KOH/gram, and the results of the elemental analyses are as follows: C 57.8%, H 4.9%, O 30.3%, and P 3.1%.

Examples 6 and 7 demonstrate that a commercial tricresylphosphate mixture can be effectively oxidized by the process of this invention. The oxidized tricresylphosphate obtained from Example 6 had a higher acid number than the material produced from Example 7 and also had a higher level of phosphorus demonstrating that catalyst staging resulted in an improved product and improved product yield.

EXAMPLE 8

Thermogravimetric Analysis of Oxidized TCP

A sample of product prepared according to the procedure presented in Example 7 was evaluated by thermogravimetric analysis using a nitrogen atmosphere and a heating rate of 10° C./minute. The results of this thermogravimetric analysis are reported in Table 3 below.

TABLE 3

| Thermogravimetric Analysis of Oxidized Tri-cresylphosphate | |
|---|---|
| Temperature °C. | Wt % Oxidized TCP Remaining |
| 330 | 57 |
| 500 | 44 |
| 700 | 40 |

A 6.1 gram sample of the product from Example 7 was heated to 150° C. under a 29" Hg vacuum in a sublimator apparatus. After 4 hours a 2.81 gram sample remained. The results of the thermogravimetric analysis of this sample are reported in Table 4 below. These data were obtained under nitrogen using a heating rate of 10° C./minute.

TABLE 4

| Temperature °C. | Wt % Oxidized TCP Remaining |
|---|---|
| 330 | 86 |
| 500 | 63 |
| 700 | 59 |
| 900 | 53 |

The thermogravimetric analysis results reported in Tables 3 and 4 demonstrate that the oxidation of tricresylphosphate by the process of this invention produced a product having substantially different thermal properties relative to the starting material, tricresylphosphate, in that significant amounts of the oxidized material remained at temperatures of 500°-900° C. In contrast, thermal gravimetric analyses of the tricresylphosphate feedstock resulted in no tricresylphosphate remaining at 330° C.

While only certain embodiments have been set forth, alternative embodiments and other modifications will be apparent from the above description to those skilled in the art. These and other alternatives are considered equivalents and within the spirit and scope of the present invention.

What is claimed is:

1. A liquid phase process for oxidizing an aryl phosphate feedstock having at least one oxidizable substituent on at least one aryl moiety, which process comprises: reacting said phosphate with a source of molecular oxygen under substantially anhydrous conditions in a reaction mixture comprising a heavy metal catalyst and a solvent comprising a lower aliphatic carboxylic acid; at a pressure sufficient to maintain said reaction mixture substantially in the liquid phase; and at an elevated temperature and for a time sufficient to oxidize at least a portion of said oxidizable substituents to aromatic carboxylic acid substituents; wherein the addition of said catalyst to said reaction mixture is staged by adding a first portion of said catalyst initially to initiate said reacting, and adding the remaining portion of said catalyst to said reaction mixture during said reacting.

2. The process of claim 1 wherein said aryl phosphate feedstock comprises a phosphate having structure:

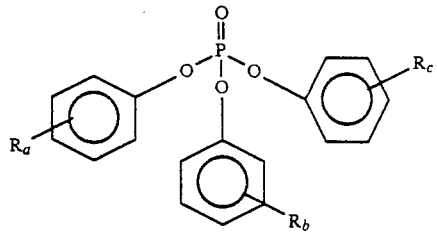

where a, b and c are each independently a number in the range of 0 to 5, inclusive, (a+b+c) being at least 1, and for each phenyl and within each phenyl R is independently selected from the group consisting of methyl, ethyl and isopropyl.

3. The process of claim 2 wherein R is independently selected from the group consisting of methyl and ethyl.

4. The process of claim 1 wherein said first portion comprises about 5 to about 50 weight percent of the total catalyst charged to said reaction mixture.

5. The process of claim 1 wherein said catalyst comprises cobalt and manganese components and further comprises a bromine promoter component.

6. The process of claim 1 wherein said catalyst comprises cobalt, manganese and nickel components, or manganese and nickel components.

7. The process of claim 5 wherein the weight ratio of cobalt (calculated as elemental cobalt) in the cobalt component of the catalyst-to-phosphate feedstock is in the range of about 0.2 to about 100 milligram atoms per gram mole of phosphate feedstock, the weight ratio of manganese (calculated as elemental manganese) in the manganese component of the catalyst-to-cobalt (calculated as elemental cobalt) in the cobalt component of the catalyst is in the range of about 0.2 to about 10 milligram atoms per milligram atom of cobalt, and the weight ratio of bromine (calculated as elemental bromine) in the bromine promoter-to-total cobalt and manganese (calculated as elemental cobalt and manganese) in the cobalt and manganese components of the catalyst is in the range of about 0.2 to about 2.0 milligram atoms per milligram atom of total cobalt and manganese.

8. The process of claim 1 wherein said anhydrous conditions are provided by a dehydrating agent comprising an anhydride of a $C_2$–$C_6$ organic carboxylic acid.

9. The process of claim 8 wherein said dehydrating agent is acetic anhydride and said solvent is acetic acid.

10. The process of claim 1 wherein said phosphate ester feedstock is tricresylphosphate (TCP).

11. A liquid phase process for oxidizing an aryl phosphate feedstock having at least one oxidizable $C_1$–$C_4$ alkyl substituent on at least one aryl moiety, which process comprises:

reacting said aryl phosphate with a source of molecular oxygen in a reaction mixture comprising cobalt, manganese and bromine catalyst components, an anhydride of a $C_2$–$C_6$ organic carboxylic acid and a solvent comprising a $C_2$–$C_6$ aliphatic monocarboxylic acid; at a pressure sufficient to maintain said reaction mixture substantially in the liquid phase; and, at a temperature and for a time sufficient to oxidize at least a portion of said oxidizable substituents and form carboxaryl phosphate product, wherein the addition of said catalyst components to said reaction mixture is staged by adding a first portion of said cobalt, manganese and bromine catalyst components to initiate said reacting, and adding the remaining portion of said catalyst components to said reaction mixture during said reacting; and recovering said carboxyaryl phosphate product from said reaction mixture.

12. The process of claim 11 wherein all of the cobalt and manganese components are added to said reaction mixture initially and all or a portion of said bromine component is added during said reacting.

13. The process of claim 11 wherein said first portion of said cobalt, manganese and bromine components comprises about 5 to about 50 weight percent of the total of cobalt, manganese and bromine charged to said reaction mixture.

14. The process of claim 11 wherein said aryl phosphate feedstock comprises a phosphate having structure:

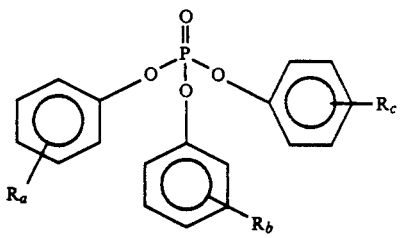

wherein a, b and c are each independently a number in the range of 0 to 2, inclusive, (a+b+c) being at least 1, and for each phenyl and within each phenyl R is independently selected from the group consisting of methyl and ethyl.

15. The process of claim 11 wherein said phosphate ester feedstock is tricresylphosphate (TCP).

16. The process of claim 14 wherein said phosphate ester feedstock is tri-meta-cresylphosphate.

17. The process of claim 14 wherein said phosphate ester feedstock is tri-para-cresylphosphate.

18. The process of claim 11 wherein said catalyst component comprises cobalt, manganese, nickel and bromine; manganese, nickel and bromine; or cobalt, cerium and bromine.

19. The process of claim 11 wherein said recovery comprises filtering a solid carboxyaryl phosphate product from said reaction mixture.

20. The process of claim 11 wherein said recovering comprises (a) adding water to said reaction mixture, (b) contacting the reaction mixture with a water-immiscible extraction solvent to extract said product, and (c) removing said extraction solvent from said so extracted product.

21. The process of claim 11 wherein said process is a semicontinuous process.

22. The process of claim 11 wherein said process is a continuous process.

* * * * *